United States Patent [19]

Sugimoto

[11] 4,296,025

[45] Oct. 20, 1981

[54] PROCESS FOR PREPARING HUMAN INTERFERON

[75] Inventor: Kaname Sugimoto, Okayama, Japan

[73] Assignee: Ken Hayashibara, Okayama, Japan

[21] Appl. No.: 149,533

[22] Filed: May 13, 1980

[30] Foreign Application Priority Data

May 24, 1979 [JP] Japan .................................. 54-63210

[51] Int. Cl.³ ........................ C07G 7/00; A61K 45/02
[52] U.S. Cl. ................................ 260/112 R; 424/85;
435/68; 435/811
[58] Field of Search ...................... 260/112 R; 424/85;
435/68, 811

[56] References Cited

U.S. PATENT DOCUMENTS 3,800,035  3/1974  Goore ..................................... 424/85
3,975,344  8/1976  Schwartz ............................... 424/85

OTHER PUBLICATIONS

Chemical Abstracts, vol. 81, p. 36, 1974, Abstract No. 149946t, Pokidysheva et al., "Stimulation of Interferon Production."
Morgensen, K., and Cantell, K., Pharm. Ther. A., vol. 1, pp. 369-381, 1977.
Sata, J., "The Current Situation of the Maintenance and Prevention of Tissue Culture Cell liner is Japan", *Protein, Nucleic Acid and Enzyme*, vol. 20, No. 4, pp. 616-643, (1975).
Strander, H. et al. "Production of Human Lymphoblastoid Interferon *Journal of Clinical Virobiology*, vol. 1, No. 1, pp. 116-117, Jan. 1975.
Miyoshi, I. et al "Human Ball, T cell and null cell leukaemic cell liner derived from ante lymphoblastic leuka-emiac, *Nature*, vol. 267, No. 5614, pp. 843-844, Jun. 30, 1977.
*Protein, Nucleic Acid and Enzyme*, vol. 21, No. 4, (1976), "Interferon-problems concerning its application".
*Cancer*, vol. 40, No. 6, Dec., 1977, Miyoshi et al., "Establishment of an Epstein-Barr Virus-Negative B—Cell...".
Klein, G., et al. "Sensitivity of Epstein-Barr Virus (EBV) Producer and non-producer human lymphoblastoid cell liner to superinfection with EB-Virus", *Int. J. Cancer*, 10, 44-57(1972).
J. L. M. "Current and Future Sources of Interferon", *Science*, vol. 204, pp. 1184-1185, Jun. 15, 1979.
Epstein, L. B. "Nitrogen and Antigen Induction of Interferon *In Vitro* and *In Vivro*", *Texas reports on biology and medicine*, vol. 35, 1977, pp. 42-56.
Chemical Abstracts, vol. 89, 105634a, 1978.
Chemical Abstracts, vol. 82, 14962u, 1975.
Chemical Abstracts, vol. 83, 25879v, 1975.
Dianzani, F., et al, "Advances in Experimental Medicine and Biology," vol. 110, pp. 119-131, 1978.

*Primary Examiner*—Delbert R. Phillips
*Assistant Examiner*—Blondel Hazel
*Attorney, Agent, or Firm*—Browdy and Neimark

[57] ABSTRACT

The present invention relates to a process for preparing a large amount of human interferon from human leukocytes. More precisely, the invention is based on the finding that the induced interferon activity can be easily increased by exposing human leukocyte suspension to both Type I and Type II interferon inducers. Thus the induced interferon activity is enhanced about 2-20-fold or higher than those attained with either Type I interferon inducer or Type II interferon inducer.

4 Claims, No Drawings

PROCESS FOR PREPARING HUMAN INTERFERON

DETAILED DESCRIPTION OF THE INVENTION

The present invention relates to a process for preparing human interferon from human leukocytes.

As described by Shigayasu Kobayashi in "Interferon," published by Kodansha Co. Ltd., Tokyo, Japan (1975), D. A. J. Tyrrell in "Interferon and Its Clinical Potential," published by William Heinemann Medical Books Ltd, London (1976), and in "Protein, Nucleic Acid and Enzyme," vol.21, no.4 (1976), interferon is a proteinaceous substance which is induced intra- or extra-cellularly by exposing live cells to interferon inducer such as virus, bacterium, protozoa, rickettsia, nucleic acid, endotoxin and polysaccharide, and which has an antiviral activity that inhibits viral multiplication nonspecies-specifically. Due to the activity, interferon has been considered as a promising prophylactic and/or therapeutic agent for viral diseases since its discovery. Recently, it has been demonstrated that interferon has an antitumor effect on non-viral tumor as well as on viral tumor, and thus the utilization of its potentiality as a medicine has been in great expectation.

It is well known that the term infferferon includes Type I interferon or classical interferon which is induced by exposing live cells to virus or nucleic acid and has a molecular weight of about $1-3\times 10^4$, and Type II interferon or immune interferon which is induced from live cells upon stimulation with mitogen or upon response to antigen and has a molecular weight of about $4-7\times 10^4$.

As described by L. E. Epstein in "Texas Report on Biology and Medicine," vol.35, page 42 (1977), published at the University of Texas Medical Branch, Galveston, Tex., U.S.A., it is well documented that Type II interferon is less stable than Type I interferon under vigorous conditions; at a pH below 2 or above 10, or at a temperature above 56° C. Since Type II interferon, however, is closely associated with immunoreaction, it is expected to be more effective than Type I interferon in the prevention and/or treatment of interferon-sensitive diseases. But interferons are highly species-specific, and only interferon from human live cells has a prophylactic and/or therapeutic effect on human diseases.

In view of these circumstances, the present inventors investigated processes for preparing a large amount of human interferon using human leukocytes as starting live human cells. The efforts resulted in the present invention that the induced interferon activity can be easily increased by exposing the human leukocyte to both Type I and Type II interferon inducers. More precisely, the induced interferon activity can be increased, by exposing human leukocyte suspension to the inducers, about 2-20-folds or more than those attained with only one of these inducers.

The human leukocyte materials usable in the invention are usually those obtained by centrifugation of peripheral blood supplied from a blood depot. Buffy coat which is available from the blood depot, ascite and bone marrow aspirate which contain a large amount of leukocyte, are also usable in the invention. In addition to the above-described materials, leukocytes obtained by culturing established human leukocytes in vitro are utilizable in the invention.

The cell suspension, prepared by suspending the human leukocytes in a physiological saline solution or a nutrient medium to give a cell concentration of about $10^4-10^8$ cells per ml and incubated at about 20°-45° C., are used for the interferon induction.

Any Type I interferon inducers can be employed in the invention as long as they induce Type I interferon; particularly for example viruses such as Sendai virus and Newcastle disease virus, double-stranded RNA and nucleic acid.

In respect to Type II interferon inducers usable in the invention, any Type II interferon inducers can be used as long as they induce Type II interferon; preferably, for example, lectins such as phytohemagglutinin and concanavalin-A, mitogens such as that of pork weed, and immunopotentiators such as lentinan, Streptococcus pyrogen, tuberculin PPD and KS-2. In addition, since antigens act as a Type II interferon inducer to the sensitized cells, antigens are advantageously feasible in the invention.

In respect to the procedures for exposing human leukocyte suspension to Type I and Type II interferon inducers, the method in which both interferon inducers are applied simultaneously, and one in which both inducers are applied successively, are both employable in the invention.

As to the interferon inducer concentration upon induction, any concentration can be applied as long as it is sufficient to induce interferon, but preferably about $0.001\ \mu g-10$ mg per ml. In this case the employment of a priming method using a highly human species-specific interferon, and a superinduction method using a metabolic inhibitor, both increase further the induced interferon activity.

The interferon thus obtained is purified and collected by conventional methods such as salting-out, dialysis, filtration, concentration, centrifugation and freeze-drying. If a further purified interferon preparation is required, it is easily obtainable by employing methods such as adsorption and desorption by ion exchanger, gel filtration, affinity-chromatography, isoelectric point fractionation and electrophoresis in combination with the above-described methods. Thus the separation and collection of both extremely highly-purified Type I and Type II interferons can be performed easily.

The interferon preparation thus obtained is advantageously feasible alone or in combination with other agents for preventing or treating human interferon-sensitive diseases including viral diseases such as epidemic keratoconjunctivitis, herpetic keratitis, influenza, rubella and serum hepatitis, and non-viral diseases such as leukemia and osteosarcoma.

The prophylactic and therapeutic agents containing interferon for the above-described interferon-sensitive diseases are preparable in various forms and phases according to their uses, for example liquid preparation for nebula, eye wash, nose drop, gargle and injection, paste preparation such as ointment, and solid preparation in powder, granule and tablet.

The activities of highly human species-specific Type I and Type II interferons were determined with human amnion FL cells described in "Protein, Nucleic Acid and Enzyme," vol.20, no.6, pp.616-643 (1975), according to the conventional plaque reduction method.

The hemagglutination titres were assayed according to the method described by J. E. Salk in "Journal of Immunology," vol.49, page 87 (1944).

EXPERIMENTs below describe the interferon prepared according to the present invention.

EXPERIMENT

To a cell suspension, prepared by suspending human leukocytes in a serum-free RPMI 1640 medium (pH 7.2) to give a cell concentration of about $1 \times 10^6$ cells per ml and kept at 37° C., was added phytohemagglutinin (about 100 μg/ml), as Type II interferon inducer, and the resulting cell mixture was incubated at this temperature for two days. Subsequently Sendai virus (about 30-hemagglutination titres/ml), as Type I interferon inducer, was added thereto, and the mixture was incubated at this temperature for an additional one day to induce interferon according to the present invention.

Control experiments 1-4 were carried out with fresh aliquots of the cell suspension as follows:

(1) Control experiment 1: A fresh aliquot of the cell suspension was added with phytohemagglutinin (about 100 μg/ml) and incubated at 37° C. for two days, but the addition of Sendai virus and the subsequent one-day-incubation of the mixture were omitted, thus control sample 1 was obtained, (2) Control experiment 2: The procedure of adding phytohemagglutinin (about 100 μg/ml) to the cell suspension and incubating the cell mixture subsequently at 37° C. for two days was repeated twice, but the addition of Sendai virus and the subsequent one-day-incubation of the mixture were totally omitted, thus control sample 2 was obtained, (3) Control experiment 3: A fresh aliquot of the cell suspension was added with Sendai virus (about 30-hemagglutination titres/ml) and incubated at 37° C. for one day, but the addition of phytohemagglutinin and the subsequent two-day-incubation of the mixture were omitted, thus control sample 3 was obtained, and (4) Control experiment 4: The procedure of adding Sendai virus (about 30-hemagglutination titres/ml) to the cell suspension and incubating the cell mixture subsequently at 37° C. for one day was repeated twice, but the addition of phytohemagglutinin and the subsequent two-day-incubation were totally omitted, thus control sample 4 was obtained.

The interferon preparations thus obtained were centrifuged and the resulting supernatants were concentrated with an ultrafilter, a cut-off molecular weight about 6,000. The components of the concentrates were fractionated according to their molecular weights by gel filtration using dextran gel, whereby Type I interferon fraction, molecular weight about 25,000, and Type II interferon fraction, molecular weight about 50,000, were obtained. The activities of both interferons were determined and the activities per ml cell suspension upon incubation were estimated. The results are as shown in the TABLE.

As obvious from the results, the combination of Sendai virus as Type I interferon inducer and phytohemagglutinin as Type II interferon inducer increased the induced interferon activities considerably in comparison with those attained with either Sendai virus or phytohemagglutinin: the present invention increased the interferon activity about 6-8-fold higher than that attained with only Sendai virus, and about 25-30-fold higher than that attained with phytohemagglutinin alone. Furthermore, the combination increased the induced Type I interferon activity about 4-5-fold higher than that induced with only the Type I interferon inducer, and the induced Type II interferon activity about 8-10-fold higher than that induced with only the Type II interferon inducer, demonstrating a remarkable synergism realized by the present invention. The combination is very advantageous for the production of interferon, especially Type II interferon.

Accordingly, the present invention for preparing human interferon wherein human leukocyte suspension is exposed simultaneously or successively to both Type I and Type II interferon inducers will play an undoubted important role in stabilizing the supply of human interferon whose potentiality is documented as well as supply is limited, and in utilizing more effectively precious blood materials.

Several embodiments according to the present invention are disclosed hereinafter.

TABLE

| Control sample No. | Interferon inducer | | Interferon activity | | |
|---|---|---|---|---|---|
| | Type I | Type II | Type I | Type II | Total |
| 1 | | P | 0 | 500 | 500 |
| 2 | | P + P | 0 | 600 | 600 |
| 3 | S | | 2,000 | 0 | 2,000 |
| 4 | S + S | | 2,500 | 0 | 2,500 |
| Present invention | S | P | 10,000 | 5,000 | 15,000 |

Note:
where S represents Sendai virus, and P represents phytohemagglutinin.

EXAMPLE 1

To 1,000 ml of a cell suspension, prepared by suspending human leukocytes in Eagle's minimal essential medium (pH 7.2) to give a cell concentration of about $5 \times 10^6$ cells per ml and kept at 37° C., was added partially-purified, highly human species-specific Type II interferon (about 100 units/ml), and the mixture was incubated for about one hour. Thereafter the cell mixture was added with concanavalin-A (500 μg/ml), and the resulting mixture was incubated at this temperature for an additional two days, followed by the addition of Sendai virus (about 100-hemagglutination titres/ml) and a 20-hour-incubation. The product, containing interferon, thus obtained was centrifuged at $1,000 \times g$ and 4° C. to remove precipitates such as cell debris, and the obtained supernatant was dialyzed for 24 hours against physiological saline solution bufferized with 0.01 M phosphate buffer to pH 7.2, and then subjected to millipore filtration. The filtrate, containing interferon, was concentrated and lyophilized into powder.

The powder product was an interferon preparation having about $1.2 \times 10^7$ units of Type I interferon activity and about $4.0 \times 10^6$ units of Type II interferon activity.

EXAMPLE 2

To 1,000 ml of a cell suspension, prepared by suspending human leukocytes in RPMI 1640 medium (pH 7.4) with 10 v/v % fetal bovine serum to give a cell concentration of about $2 \times 10^7$ cells per ml and kept at 35° C., was added phytohemagglutinin (about 200 μg/ml), and the cell mixture was incubated at this temperature for 3 days. Thereafter the cell mixture was added with Newcastle disease virus (about 300-hemagglutination titres/ml) which was pre-inactivated by UV-irradiation, and the resulting mixture was incubated at this temperature for an additional 24 hours. The product, containing interferon, was centrifuged at 1,000× g and 4° C. to remove precipitates such as cell debris, and the resulting supernatant was dialyzed for 20 hours against physiological saline solution bufferized with 0.01 M phosphate buffer to pH 7.2, followed by millipore filtration. The filtrate, containing interferon, was concentrated.

The concentrate was an interferon preparation having about $7.0 \times 10^7$ units of Type I interferon activity and about $2.3 \times 10^7$ units of Type II interferon activity.

EXAMPLE 3

To 2,000 ml of a cell suspension, prepared by suspending buffy coat in a serum-free RPMI 1640 medium (pH 7.2) to give a cell concentration of about $5 \times 10^5$ cells per ml and kept at 38° C., was added Maruyama vaccine (about 1 μg/ml) and Sendai virus (about 20-hemagglutination titres/ml), and the resulting cell mixture was incubated at this temperature for 2 days. The product, containing interferon, was purified and lyophilized into powder similarly as in EXAMPLE 1.

The powder product was an interferon preparation having about $5.0 \times 10^6$ units of Type I interferon activity and about $1.0 \times 10^6$ units of Type II interferon activity.

EXAMPLE 4

To 1,000 ml of a cell suspension, prepared by suspending buffy coat in Eagle's minimal essential medium (pH 7.2) with 5 v/v % human serum to give a cell concentration of about $1 \times 10^7$ cells per ml and kept at 37° C., was added tuberculin PPD (10 μg/ml), and the resulting cell mixture was incubated at this temperature for 2 days, followed by the addition of a synthetic polyinosinic:polycytidylic acid (poly I:poly C) (5 μg/ml) and further 10-hour-incubation. The product, containing interferon, was purified and concentrated similarly as in EXAMPLE 2.

The concentrate was an interferon preparation having about $2.0 \times 10^7$ units of Type I interferon activity and about $6.0 \times 10^6$ units of Type II interferon activity.

EXAMPLE 5

To 1,000 ml of a cell suspension, prepared by suspending human leukocytes in RPMI 1640 medium (pH 7.2) with 5 vv % human serum to give a cell concentration of about $1 \times 10^6$ cells per ml and kept at 37° C., was added KS-2, an immunopotentiator derived from *Lentinus edodes* mycelium, and the cell mixture was incubated at this temperature for 2 days, followed by the addition of Sendai virus (about 50-humagglutination titres/ml) and an additional 20-hour-incubation. The product, containing interferon, was purified and lyophilized into powder similarly as in EXAMPLE 1.

The powder product was an interferon preparation having about $3.0 \times 10^6$ units of Type I interferon activity and about $1.5 \times 10^6$ units of Type II interferon activity.

What we claim is:

1. A process for preparing human interferon, comprising exposing human leukocyte suspension to both Type I and Type II interferon inducers to induce interferon, and purifying and collecting the induced interferon.

2. A process as set forth in claim 1, wherein said exposure is carried out simultaneously or successively with interferon inducer concentrations of 0.001 μg–10 mg per ml and leukocyte concentration of $10^4$–$10^8$ cells per ml at a temperature in the range of 20°–45° C.

3. A process as set forth in claims 1 or 2, wherein a material selected from the group consisting of peripheral blood, buffy coat, ascite, bone marrow aspirate and human leukocytes obtained by culturing established human leukocytes in vitro is used as human leukocyte source.

4. A process as set forth in claims 1 or 2, wherein said Type I interferon inducer is selected from the group consisting of Sendai virus, Newcastle disease virus, double-stranded RNA and nucleic acid, and said Type II interferon inducer is selected from the group consisting of lectins including phytohemagglutinin and concanavalin-A, mitogens including that of pork weed, and immunopotentiators including lentinin, Maruyama vaccine, Streptococcus pyrogen, tuberculin PPD and KS-2.

* * * * *